United States Patent [19]
Avalle

[11] Patent Number: 6,080,424
[45] Date of Patent: Jun. 27, 2000

[54] COSMETIC POWDERS COATED WITH NATURAL INGREDIENTS

[75] Inventor: Nadia Avalle, Milan, Italy

[73] Assignee: Intercos Italia S.p.A., Milan, Italy

[21] Appl. No.: 09/065,453

[22] Filed: Apr. 24, 1998

[30] Foreign Application Priority Data

Apr. 24, 1997 [IT] Italy .................................. MI97A0956

[51] Int. Cl.⁷ .............................. A61K 9/127; A61K 9/14
[52] U.S. Cl. ............................................ 424/450; 424/489
[58] Field of Search ................................ 424/401, 69, 61, 424/489, 450; 514/845, 844, 846

[56] References Cited

U.S. PATENT DOCUMENTS 4,609,545  9/1986  Schlossman .............................. 424/63
4,622,074  11/1986  Miyoshi et al. ..................... 106/308 F

*Primary Examiner*—Thurman K. Page
*Assistant Examiner*—S. Howard
*Attorney, Agent, or Firm*—Jacobson, Price, Holman & Stern, PLLC

[57] ABSTRACT

The invention refers to a powder coated with natural ingredients and a cosmetic composition containing one or more of such powders. The powder contains 0.1–99.0% of a powder phase, 0.01–10% of a phospholipid phase and 0.005–5% of a protein phase.

6 Claims, No Drawings

COSMETIC POWDERS COATED WITH NATURAL INGREDIENTS

DESCRIPTION

The present invention refers to the preparation of a powder coated with natural ingredients similar to the components of biological membranes and to the employment of such powders in cosmetic make-up products.

Make-up cosmetics, as for example foundations, blushers, eye shadows, lipsticks, etc., that are used to give colour to skin and lips, are largely composed of inorganic powders. When these products are applied to the skin they create a coloured film that masks skin defects and gives a visually more uniform appearance to it. This film is simply deposited on the surface of the skin, therefore inorganic powders come directly into contact with the superficial layers of the epidermis.

Sometimes the direct contact of inorganic powders with the skin produces phenomena of absorption of the water present on the surface of the skin and a consequent unpleasant feel on behalf of the user of the cosmetic product, with antiaesthetic and sometimes irritating effects.

The main object of the present invention is the preparation of a powder coated with natural ingredients similar to the components of biological membranes that by interposing themselves between the powder and the cuticle epidermal layer partially or totally prevent the direct contact with the skin.

An additional object of this invention is a coating consisting of phospholipids and proteins, which as it is known are the main components of cellular membranes, in ratios comprised between 1:100 and 100:1, preferably phospholipids and proteins with natural origin, more preferably phospholipids with vegetable origin, and even more preferably a lecithin with a high content of phosphatidic acid as a phospholipide and zein as a protein.

An additional object of the present invention is the employment of such coated powders in cosmetic make-up product.

According to the present invention a composition suitable to form a powder with its respective coating is characterised in that it contains the following ingredients:

a) 0.1–99.0% of a powder phase,
b) 0.01–10% of a phospholipid phase,
c) 0.005–5% of a protein phase.

The powder phase can be composed of various excipients used traditionally in cosmetics: talcum, mica, kaolin, starch, zinc oxide, nylon-12, polyethylene, silica, spherical silicon dioxides, acrylate polymers and copolymers, etceteras, alone or as a mixture of them or in a combination with pigments such as iron oxides, chromium oxides, ultramarine blue, ultramarine pink, manganese violet, titanium dioxide, mica and titanium dioxide base pearls, mica and bismuth oxychloride base pearls, carmine, lakes and organic dye base pigments such as CTFA.

This phase can also be bonded to the powders by means of a metallic water soluble salt. Soluble salts of Al, Mg, Ca, Zn, Zr and Ti are some example of these salts. The phospholipid phase can be composed of various phospholipids or of lipids in which glyceril is esterified with phosphoric acid that can itself be esterified with a second alcohol. Some examples of phospholipids are: phosphatidic acid, phosphatidylcoline (lecithin), phosphatidilethanolamine, etc. In commercial terminology, mixture of different types of phospholipids can be found under the term of lecithin. In this invention lecithins with natural origin are preferred, the ones with vegetable origin being more preferred, and even more preferred the ones with a high content of phosphatidic acid.

The protein phase can be composed of various types of proteins that are acceptable for cosmetic use, preferably by natural proteins, more preferably by vegetable proteins, even more preferably by zein.

According to the invention the composition of a cosmetic make-up product which employs such coated powders in the following percentages is claimed:

a) 0.1–99.9% of a coated powder phase as described above
b) 0.1–99.9% of other cosmetically acceptable components.

The composition of this invention provides for the use of 0.1–99% of other cosmetically acceptable components such as oils, waxes, surfactants, silicones, perfluorides, other non-coated or differently coated powder, fragrances, dyes or coloured pigments, or other base materials as CTFA. The base materials with natural origin are preferred in this invention, the ones with vegetable origin being more preferred.

EXAMPLE 1

1492 g of talcum are added under mechanical agitation to 5 liters of a 0.1% $Al_2(SO_4)_3$ water base solution. The mixture is let react for 15' at 50° C. until a homogeneous dispersion is obtained. 15.5 g of lecithin pre-dispersed in 60 g of water with pH=9 are slowly added to the mixture. At the end of the addition, the system is let react for 15' at 50° C., filtered under vacuum, and dried in an oven at 80° C. 3 g of Zein pre-solubilised in 4.5 g of water and 25.5 g of EtOH are atomised on the talcum that is maintained in agitation in a propeller mill. The product is exsiccated in an oven at 80° C. until dry.

EXAMPLE 2

1492 g of yellow iron oxide pre-treated with mica at 30% are maintained in suspension in a propeller mill (3000 revolutions/minute). 100 g of a 5.6% $Al_2(SO_4)_3$ solution are added by atomisation. Subsequently and without interrupting the procedure 150 g of a 10% lecithin solution with pH=9 and 30 mil of a 10% Zein solution are atomised. The product is dried in an oven at 80° C. under vacuum and it is passed through a 200 mesh sifter. A second phospholipid layer can be deposited on the powder by atomising 150 g of a 10% lecithin solution on the powder maintained in agitation in the mill. The product is dried in an oven at 90° C. under vacuum.

EXAMPLE 3

A cosmetic powder has been prepared according to the following formula, by employing powders and pigments coated with the same process as in example 1 or 2.

| | |
|---|---|
| Coated talcum/mica (70/30) | 77.4 |
| Coated titanium dioxide CI 77891 | 2.24 |
| Coated yellow iron oxide/mica (70/30) | 1.6 |
| Coated red iron oxide/mica (70/30) | 0.16 |
| Coated brown iron oxide/mica (70/30) | 0.8 |
| Silica | 4.5 |
| Nylon-12 | 3 |
| Isononaned isononyl | 3.1 |
| Isostearyl lactate | 6 |

-continued

| | |
|---|---|
| Fragrance | 0.2 |
| Preservative | 1 |
| | 100.00 |

EXAMPLE 4

A pressed powder foundation has been prepared according to the following formula, by employing powders and pigments coated with the same process as in example 1 or 2.

| | |
|---|---|
| Coated talcum/mica (70/30) | 61.4 |
| Coated titanium dioxide CI 77891 | 6 |
| Coated yellow iron oxide/mica (70/30) | 1.0 |
| Coated red iron oxide/mica (70/30) | 0.6 |
| Coated brown iron oxide/mica (70/30) | 1.8 |
| Silica | 4.5 |
| Nylon-12 | 6 |
| Active ingredient compound | 1.4 |
| Pearls (titanium dioxide/mica) | 5 |
| Myristate magnesium | 2 |
| Isononaned isononyl | 3.5 |
| Fatty acids C8–10 triglyceride | 5 |
| Fragrance | 0.2 |
| Preservative | 1 |
| | 100.00 |

I claim:

1. Coated powder comprising the following ingredients:

a) 0.1–99.0% of a powder phase, b) 0.01–10% of a phospholipid phase consisting essentially of natural lecithin, and c) 0.005–5% of a protein phase.

2. Coated powder according to claim 1, wherein said phospholipid phase is partially or totally absorbed on the surface by means of a water soluble metallic salt.

3. Coated powder according to claim 2, wherein the phospholipid phase is partially absorbed on the surface by means of at least one water soluble metallic salt selected from the group consisting of Al, Mg, Ca, Zn, Zr and Ti soluble salts.

4. Coated powder according to claim 1, wherein the protein phase includes zein.

5. Cosmetic composition containing one or more powders according to claim 1, wherein cosmetically acceptable components are included in the following percentages:

a) 0.1–99.99% of a coated powder phase; and b) 0.1–99.9% of cosmetically acceptable components.

6. A cosmetic make-up composition containing one or more powders according to claim 1.

* * * * *